United States Patent
Kim et al.

(10) Patent No.: US 10,550,442 B2
(45) Date of Patent: Feb. 4, 2020

(54) METHOD FOR DIAGNOSING PREMATURE DELIVERY IN A PREGNANT WOMAN

(71) Applicants: EWHA UNIVERSITY-INDUSTRY COLLABORATION FOUNDATION, Seoul (KR); DANKOOK UNIVERSITY CHEONAN CAMPUS INDUSTRY ACADEMIC COOPERATION FOUNDATION, Chungcheongnam-do (KR)

(72) Inventors: Yoon-Keun Kim, Paju-si (KR); Young-Ju Kim, Seoul (KR); Young Koo Jee, Seongnam-si (KR); Mina Rho, Seoul (KR); Byung-In Moon, Seoul (KR); Minhye Kim, Seoul (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 15/552,896

(22) PCT Filed: Feb. 19, 2016

(86) PCT No.: PCT/KR2016/001665
§ 371 (c)(1),
(2) Date: Aug. 23, 2017

(87) PCT Pub. No.: WO2016/137164
PCT Pub. Date: Sep. 1, 2016

(65) Prior Publication Data
US 2018/0057896 A1 Mar. 1, 2018

(30) Foreign Application Priority Data
Feb. 23, 2015 (KR) .................. 10-2015-0025381

(51) Int. Cl.
| C12N 9/96 | (2006.01) |
| C12R 1/07 | (2006.01) |
| A61K 35/74 | (2015.01) |
| C12N 1/20 | (2006.01) |
| C12Q 1/686 | (2018.01) |
| G01N 33/574 | (2006.01) |

(52) U.S. Cl.
CPC ............... *C12R 1/07* (2013.01); *A61K 35/74* (2013.01); *C12N 1/20* (2013.01); *C12Q 1/686* (2013.01); *G01N 33/57415* (2013.01)

(58) Field of Classification Search
None
See application file for complete search history.

(56) References Cited

U.S. PATENT DOCUMENTS

2014/0141102 A1   5/2014   Garfield et al.

FOREIGN PATENT DOCUMENTS

| KR | 10-2009-0123875 A | 12/2009 |
| KR | 10-2011-0025603 A | 3/2011 |
| KR | 10-2011-0082481 A | 7/2011 |
| KR | 10-2012-0084900 A | 7/2012 |

OTHER PUBLICATIONS

Harrison et al. ("Extracellular Vesicles in Health and Disease", 2014, pp. 1-455).*
Perez-Munoz et al. (Microbiome, 5(48), 2017, pp. 1-19).*
Van der Pol et al. (Pharmacol. Rev., 2012, vol. 64, No. 3, pp. A-AD).*
Yoo et al., "16S rRNA gene-based metagenomic analysis reveals differences in bacteria-derived extracellular vesicles in the urine of pregnant and non-pregnant women", Experimental & Molecular Medicine, vol. 48, e208, 9 pages, (2016).
Agerholm et al., "Experimental infection of pregnant cows with Bacillus licheniformis bacteria", Vet Pathol., 1999, vol. 36(3), pp. 191-201.
Smith et al., "Further data on the effect of vaccination against bovine infectious abortion", The Journal of experimental medicine, 1926, vol. 43(3), pp. 327-330.

* cited by examiner

*Primary Examiner* — Hope A Robinson
(74) *Attorney, Agent, or Firm* — Vorys, Sater, Seymour and Pease LLP; Mih Suhn Koh

(57) ABSTRACT

Provided is a composition for the treatment of pregnancy-associated diseases, and more particularly, to a pharmaceutical composition for the prevention or treatment of premature delivery or breast cancer. The pharmaceutical composition including extracellular vesicles derived from bacteria belonging to the genus *Bacillus* as an active ingredient may induce pregnancy or prevent premature delivery of pregnant women, may be used to prevent or treat pregnancy-associated diseases such as breast cancer, and may be used to diagnose a risk of premature delivery by measuring the amount of extracellular vesicles derived from bacteria belonging to the genus *Bacillus* in pregnant women.

3 Claims, 13 Drawing Sheets
Specification includes a Sequence Listing.

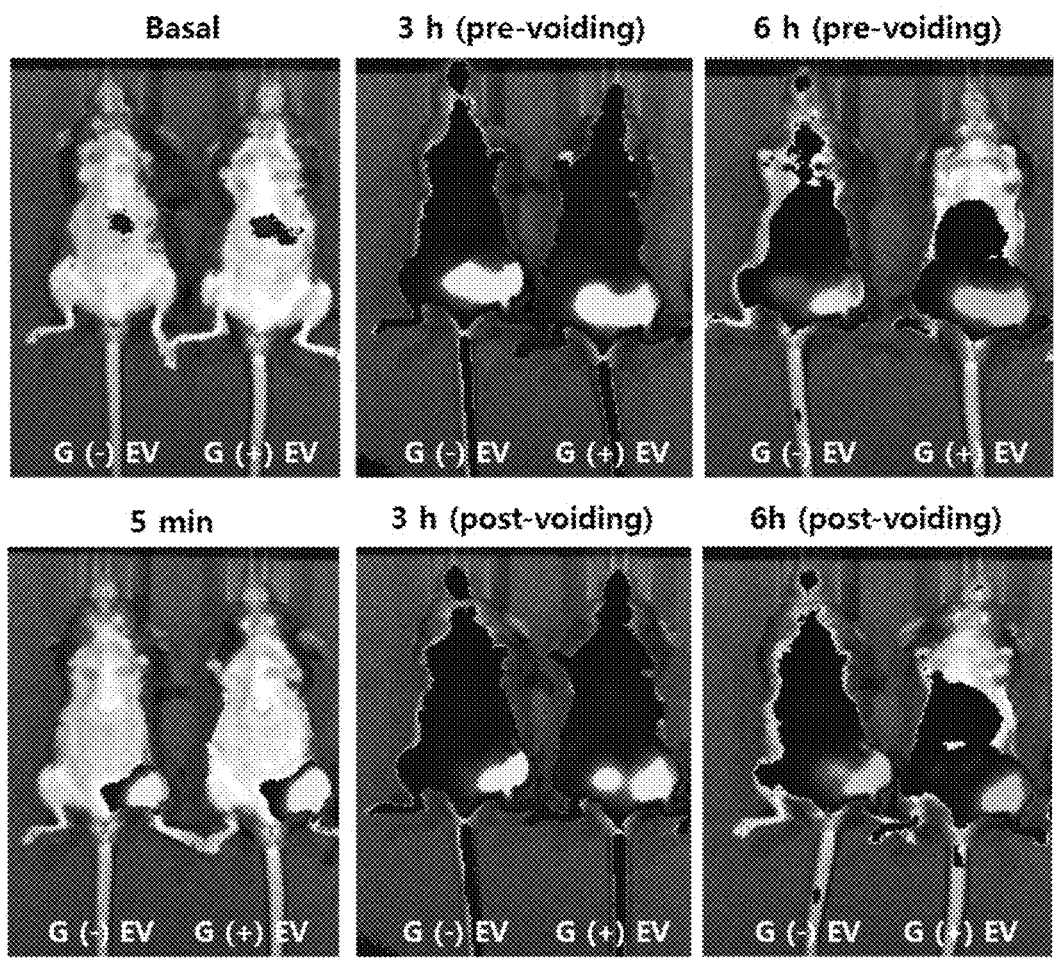

[Fig. 1B]
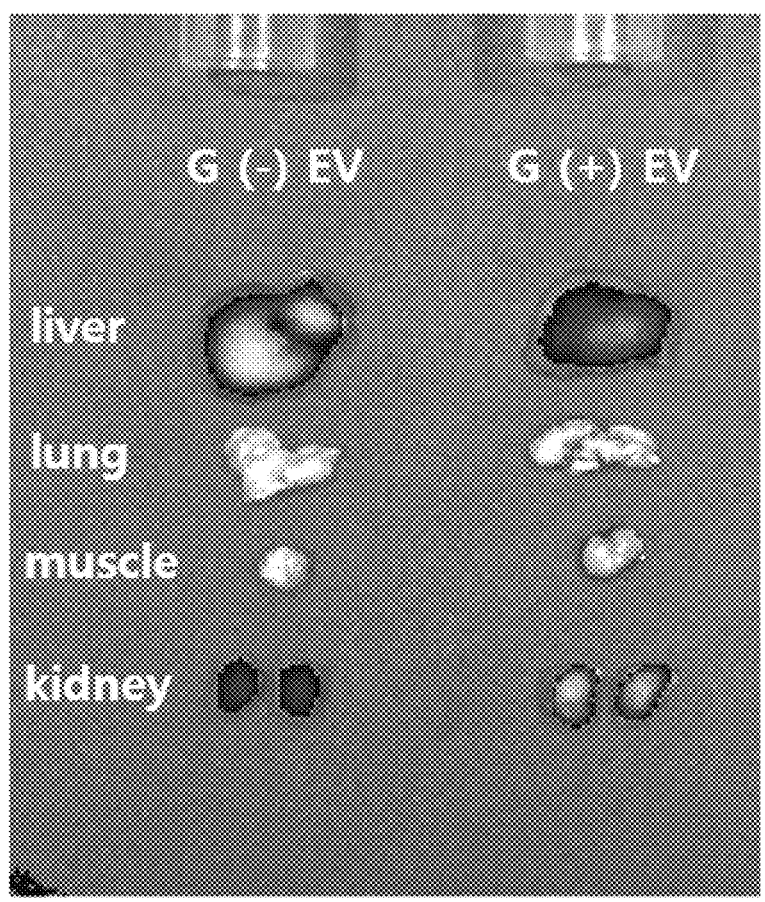

[Fig. 2]
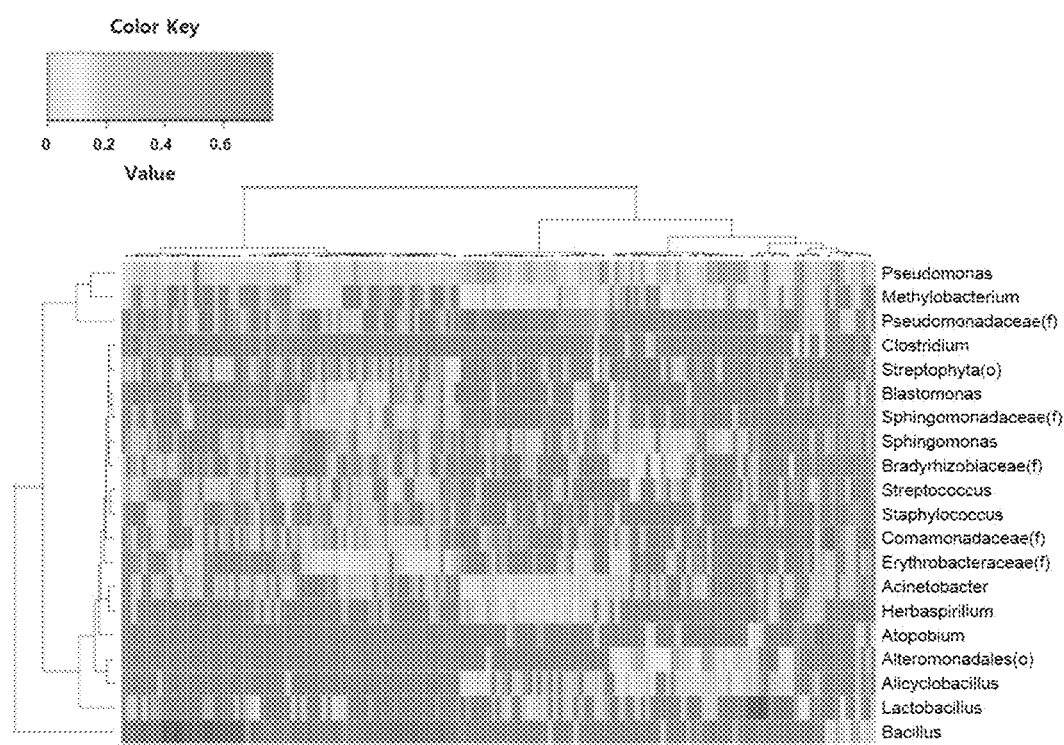

[Fig. 3A]
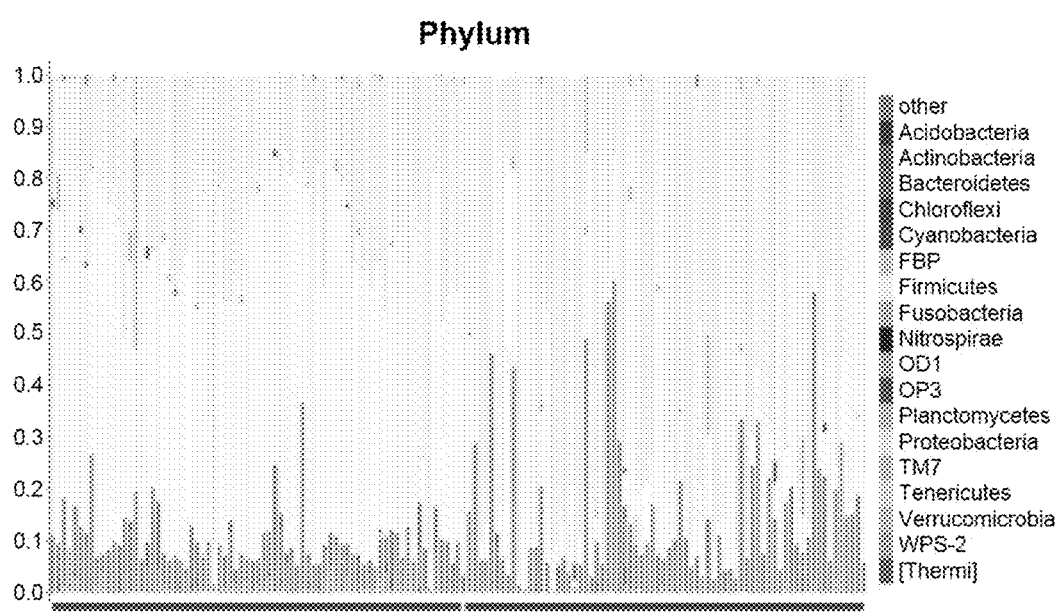

[Fig. 3B]
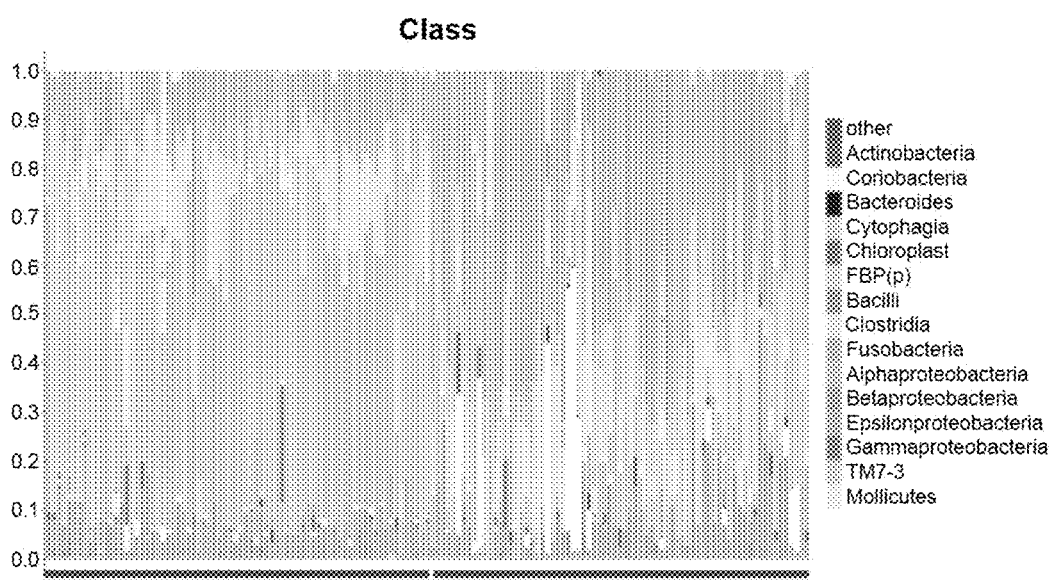

[Fig. 3C]

[Fig. 3D]
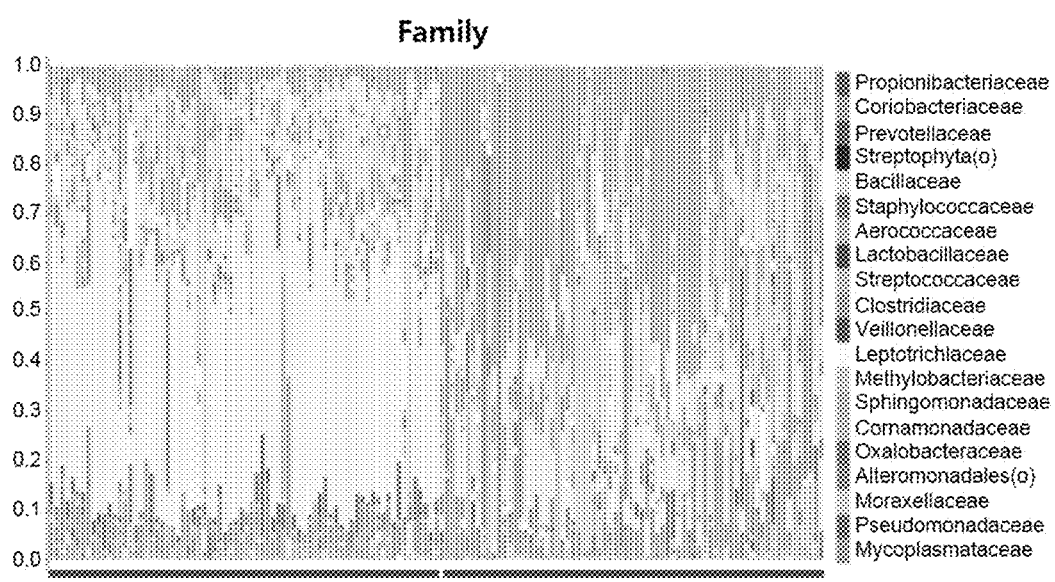

[Fig. 4]
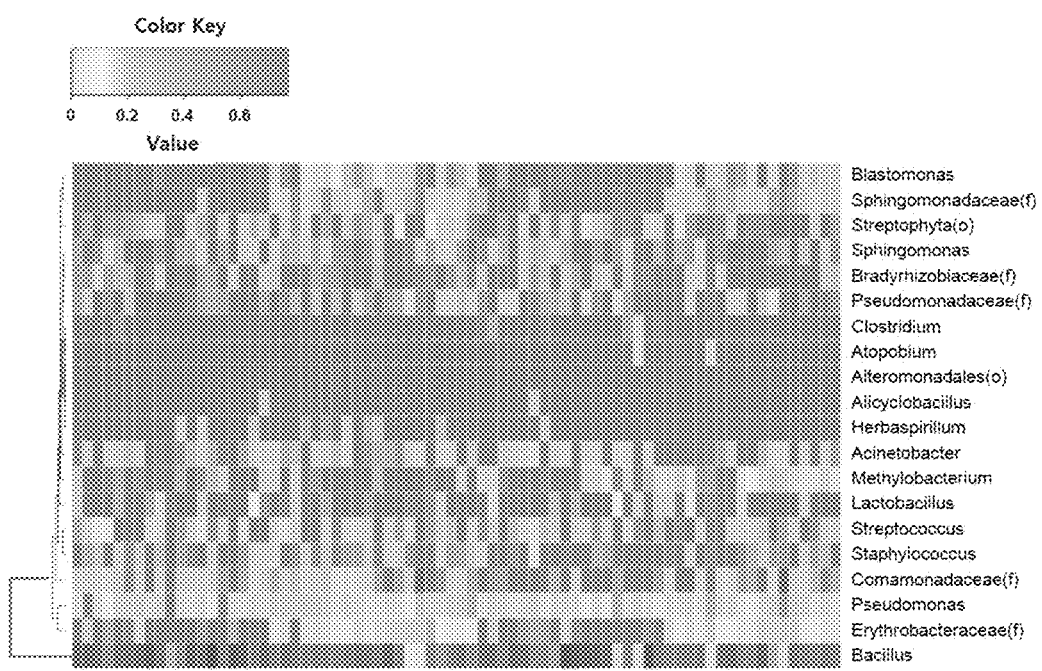

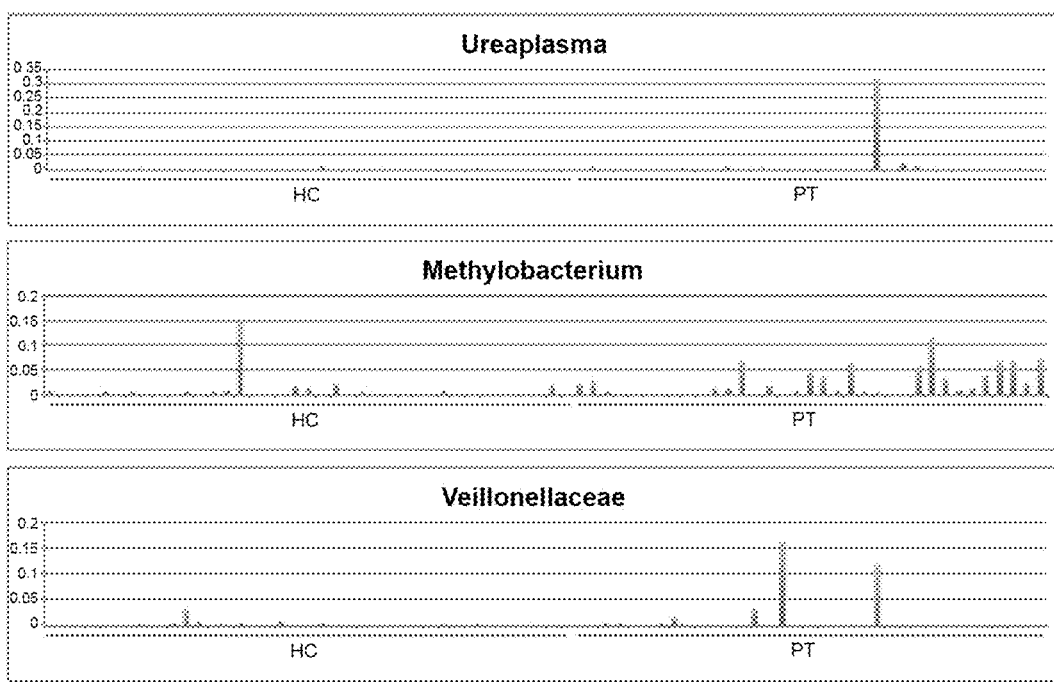
[Fig. 5]

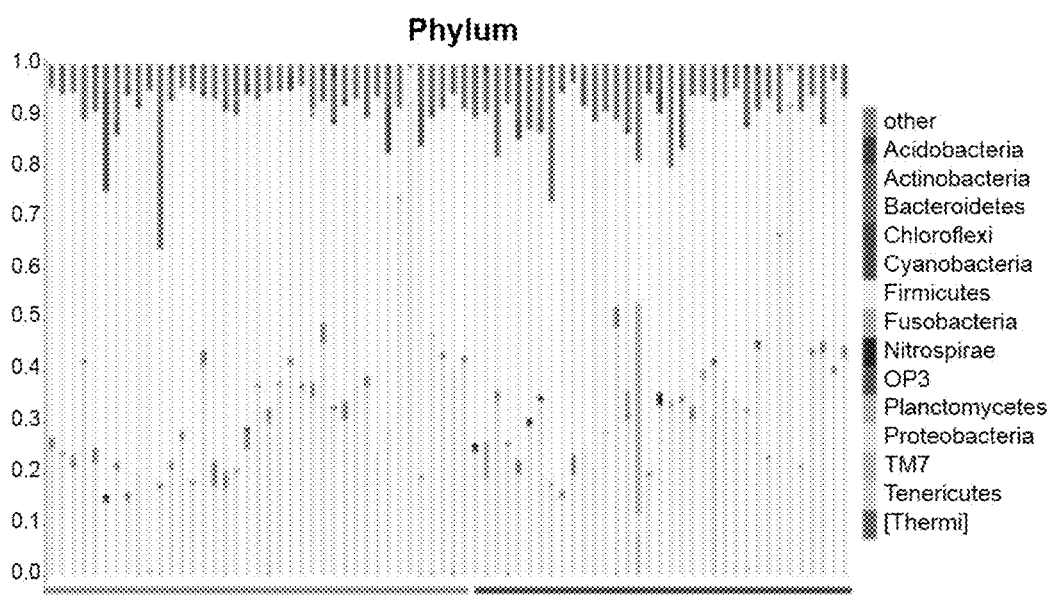
[Fig. 6A]

[Fig. 6B]
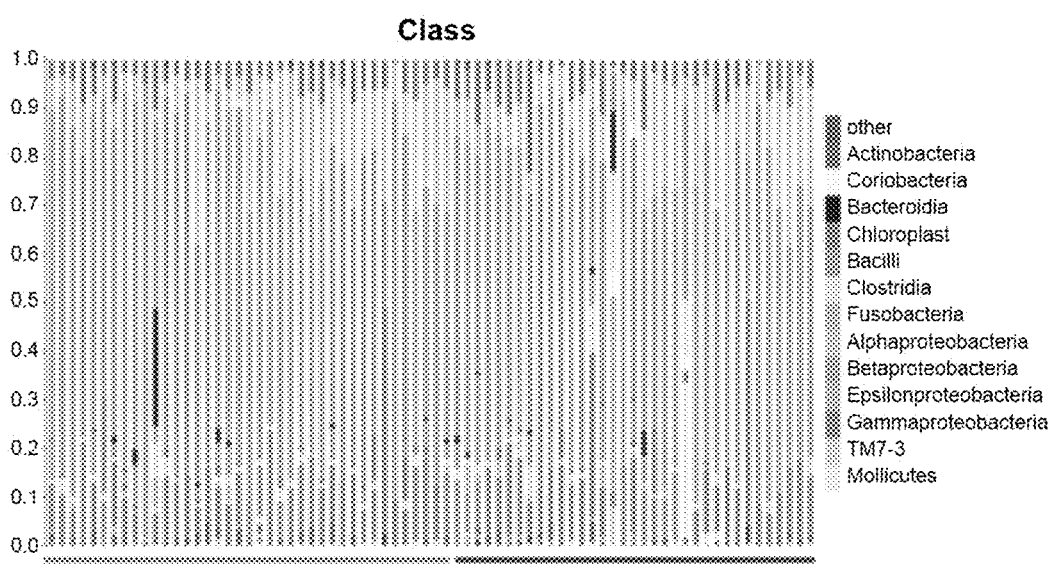

[Fig. 6C]

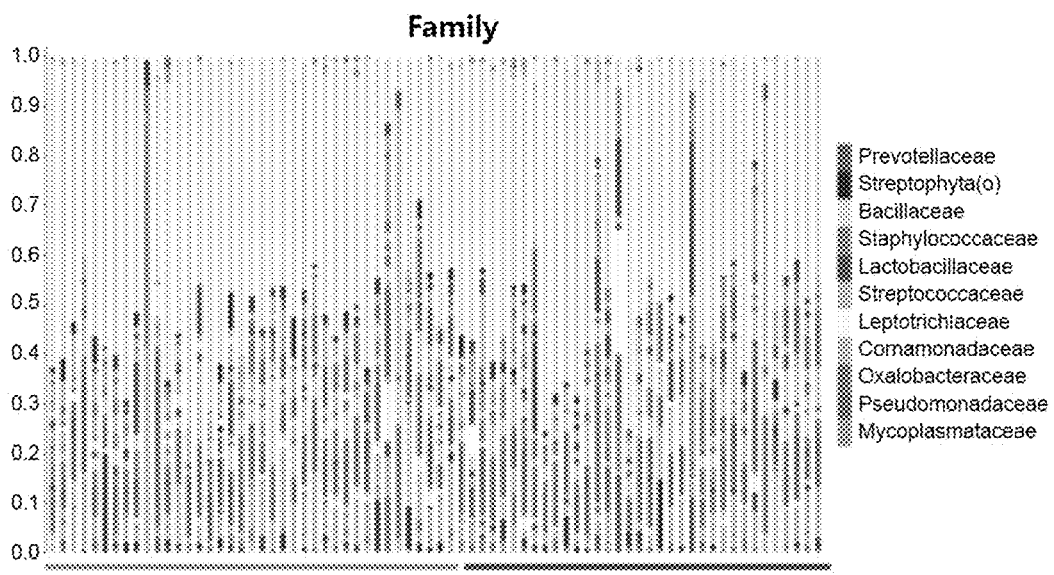
[Fig. 6D]

METHOD FOR DIAGNOSING PREMATURE DELIVERY IN A PREGNANT WOMAN

STATEMENT REGARDING GOVERNMENT RIGHTS

The present invention was undertaken with the support of Development of nanovesicle based preventive vaccine against Scrub typhus No. HI16C0998 grant funded by Korea Health Industry Development Institute.

CROSS-REFERENCE TO RELATED APPLICATION

This application claims priority to and the benefit of Korean Patent Application No. 10-2015-0025381, filed on Feb. 23, 2015 and International Patent Application No. PCT/KR2016/001665, filed on Feb. 19, 2016, the disclosure of which are incorporated herein by reference in their entirety.

SEQUENCE LISTING

The Sequence Listing submitted in text format (.txt) filed on Aug. 23, 2017, named "SequenceListing.txt", created on Aug. 18, 2017, 766 bytes), is incorporated herein by reference.

TECHNICAL FIELD

The present invention relates to a composition for the treatment of pregnancy-associated diseases, and more particularly, to a pharmaceutical composition for the prevention or treatment of premature delivery or breast cancer, including extracellular vesicles derived from bacteria belonging to the genus *Bacillus* as an active ingredient, and a method of diagnosing premature delivery.

BACKGROUND ART

Bacteria secrete nanometer-sized extracellular vesicles (EVs) into the extracellular environment for intercellular information exchange. Gram-negative bacteria-derived EVs, or outer membrane vesicles (OMVs) are spherical bilayered proteolipids, are often referred to as nanovesicles, and contain lipopolysaccharides, toxic proteins, and DNA and RNA which are nucleic acids of bacteria. Gram-positive bacteria-derived EVs also contain peptidoglycan and lipoteichoic acid, which are cell wall components of bacteria, in addition to toxic proteins and nucleic acids. According to recent studies, it has been reported that such bacteria-derived EVs play a vital role in the occurrence of inflammation diseases which have been believed to be noninfectious.

Meanwhile, it is known that around 15 million newborn babies are born each year as premature babies worldwide, and these account for a tenth or more of the number of the world's newborn babies. Such premature delivery is known to be caused by infections (urinary tract infections and vaginal infections), malformations of the uterus and uterine cervix, external fertilization, nourishment of pregnant women, and genetic factors. In addition, many researchers suggest that intrauterine infections are an important mechanism for explaining 25% to 40% of premature delivery. Pregnant women undergo anatomical, physiological and biochemical changes due to hormonal and physical changes. For example, *Lactobacillus acidophilus* increases, and, as a result, vaginal secretion increases and vaginal pH decreases. Thus, through pregnancy-associated microorganism studies, information on cytokine degree, pH changes, a difference in vulnerability to infection, and the like of the vagina and amniotic fluid of pregnant and non-pregnant women may be acquired.

Breast cancer is the second most cancer occurring in Korean women, and was ranked second with about 15% of an annual average number of cancer occurrence cases between 1999 and 2002. Globally, breast cancer occurs at a much higher rate in western people living in the USA, Europe, and Australia than in Asian people. Although female breast cancer in South Korea is at a much lower level than in western people, the fact that women living in a so-called westernized environment of big cities have a high incidence rate and epidemiological phenomena in which the occurrence of breast cancer tends to continuously increase compared to the past may mean that factors causing the occurrence of breast cancer are continuously inherent in the South Korean women population and are accelerating cancer occurrence. It is known that the earlier age at menarche or the later age at menopause results in the blood estrogen concentration according to a regular menstruation cycle being maintained at a higher rate, and thus a risk for breast cancer becomes higher. In addition, it is known that women with early ages at the first full term delivery have a decreased risk for breast cancer 10 years after delivery, and women with high fertility also have a low risk for breast cancer. In contrast, it is known that women having never experienced childbirth have the highest risk for breast cancer, but an accurate mechanism for effects of pregnancy on the prevention of breast cancer has not yet been discovered. Primary prevention for preventing the occurrence of breast cancer itself includes suppression of the carcinogenic environment, and changes in health behaviors and habits of individuals. For example, a method of delaying ages at menarche as late as possible by suppressing obesity or an aggressive prevention method using drugs such as hormones and the like may also be considered.

Metagenomics, also called environmental genomics, is analytics for metagenomic data obtained from samples collected from the environment. Recently, the bacterial composition of human microbiota has been listed using a method based on 16s ribosomal RNA (16s rRNA) base sequences, and 16s ribosomal RNA base sequences are analyzed using a 454FLX titanium platform. There have been studies on metagenomes analyzed in feces, vaginal secretion, and amniotic fluid of pregnant women, but there have never been studies on bacterial metagenomic analysis during pregnancy in urine because urine has been regarded as bacterial-free.

In addition, to date, there have been no cases of using bacteria-derived EVs for the induction of pregnancy or the prevention of premature delivery, and for the prevention or treatment of breast cancer.

DISCLOSURE

Technical Problem

The inventors of the present invention performed metagenomic analysis using DNA of extracellular vesicles derived from urine of non-pregnant women and pregnant women and, as a result, verified that extracellular vesicles derived from bacteria belonging to the genus *Bacillus* were significantly increased in pregnant women, in particular, women having undergone normal delivery, thus completing the present invention.

Therefore, an object of the present invention is to provide a pharmaceutical composition for the prevention or treatment of pregnancy-associated diseases such as premature delivery or breast cancer, the pharmaceutical composition including extracellular vesicles derived from bacteria belonging to the genus *Bacillus* as an active ingredient.

Another object of the present invention is to provide a method of diagnosing premature delivery.

However, the technical goals of the present invention are not limited to the aforementioned goals, and other unmentioned technical goals will be clearly understood by those of ordinary skill in the art from the following description.

Technical Solution

To achieve the above technical goals of the present invention, the prevent invention provides a pharmaceutical composition for preventing or treating pregnancy-associated diseases, the pharmaceutical composition including extracellular vesicles derived from bacteria belonging to the genus *Bacillus* as an active ingredient.

In one embodiment of the present invention, the extracellular vesicles may be isolated from cultures of bacteria belonging to the genus *Bacillus* or foods fermented with bacteria belonging to the genus *Bacillus*.

In another embodiment of the present invention, the extracellular vesicles are naturally or artificially secreted from bacteria belonging to the genus *Bacillus*.

In yet another embodiment of the present invention, the extracellular vesicles have an average diameter of 20 nm to 300 nm.

In still another embodiment of the present invention, the pregnancy-associated diseases may be premature delivery.

In still another embodiment of the present invention, the pregnancy-associated diseases may be breast cancer.

The present invention also provides a composition for inducing normal pregnancy, the composition including extracellular vesicles derived from bacteria belonging to the genus *Bacillus* as an active ingredient.

In one embodiment of the present invention, the extracellular vesicles may be isolated from cultures of bacteria belonging to the genus *Bacillus* or foods fermented with bacteria belonging to the genus *Bacillus*.

In another embodiment of the present invention, the extracellular vesicles are naturally or artificially secreted from bacteria belonging to the genus *Bacillus*.

In yet another embodiment of the present invention, the extracellular vesicles have an average diameter of 20 nm to 300 nm.

The present invention also provides a method of diagnosing premature delivery, the method including the following processes:

(A) extracting 16s rDNA from extracellular vesicles isolated from urine samples of pregnant women;

(B) performing a polymerase chain reaction (PCR) on the 16s rDNA using a primer pair having sequences of SEQ ID NOS: 1 and 2; and (C) determining that, in a case in which distribution of extracellular vesicles derived from bacteria belonging to the genus *Bacillus* is at least two times lower than that in normal pregnant women through sequencing of a product of the PCR, the case has a high risk of premature delivery.

In one embodiment of the present invention, in process (A), isolation of the extracellular vesicles includes the following processes:

(a) boiling each urine sample for 10 minutes to 30 minutes and then cooling the boiled urine sample;

(b) centrifuging the cooled product to obtain a supernatant; and (c) sequentially filtering the supernatant through a 0.45 μm filter and a 0.22 μm filter.

In another embodiment of the present invention, the extracellular vesicles have an average diameter of 20 nm to 300 nm.

The present invention also provides a method of preventing or treating pregnancy-associated diseases, the method including administering, to an individual, a composition comprising extracellular vesicles derived from bacteria belonging to the genus *Bacillus* as an active ingredient.

The present invention also provides a use of extracellular vesicles derived from bacteria belonging to the genus *Bacillus* for the prevention or treatment of pregnancy-associated diseases.

The present invention also provides a use of extracellular vesicles derived from bacteria belonging to the genus *Bacillus* for the diagnosis of premature delivery.

Advantageous Effects

According to the present invention, a pharmaceutical composition including extracellular vesicles derived from bacteria belonging to the genus *Bacillus* as an active ingredient can induce pregnancy or prevent the premature delivery of pregnant women, can be used to prevent or treat pregnancy-associated diseases such as breast cancer, and can be usefully used to diagnose a risk of premature delivery by measuring the amount of extracellular vesicles derived from bacteria belonging to the genus *Bacillus* in pregnant women.

DESCRIPTION OF DRAWINGS

FIGS. 1A and 1B are images obtained to confirm whether extracellular vesicles derived from *Escherichia coli* as gram-negative bacteria and *Staphylococcus aureus* as gram-positive bacteria were excreted via urine after being administered to mice via muscular injection, and respectively showing whole-body in vivo fluorescence images and specific in vivo fluorescence images of organs of the mice extracted at 21 hours after administration of the extracellular vesicles.

FIG. 2 illustrates a variety of classification groups of bacteria-derived extracellular vesicles isolated from urine of pregnant women (left side) and non-pregnant women as a normal control (right side).

FIGS. 3A to 3D respectively illustrate phylum-level analysis results, class-level analysis results, order-level analysis results, and family-level analysis results of constituent ingredients of bacteria-derived extracellular vesicles isolated from urine of non-pregnant women as a normal control (blue underline, right side) and pregnant women (red underline, right side).

FIG. 4 illustrates distribution results of bacteria-derived extracellular vesicles isolated from urine of a normal delivery group and a premature delivery group.

FIG. 5 illustrates summary results of the distribution of bacteria-derived extracellular vesicles isolated from urine of a normal delivery group and a premature delivery group.

FIGS. 6A to 6D respectively illustrate phylum-level analysis results, class-level analysis results, order-level analysis results, and family-level analysis results of the distribution of bacteria-derived extracellular vesicles isolated from urine of a normal delivery group (green underline, left side) and a premature delivery group (purple underline, right side).

BEST MODE

The present invention provides a pharmaceutical composition for the prevention or treatment of pregnancy-associated diseases which includes extracellular vesicles derived from bacteria belonging to the genus *Bacillus* as an active ingredient.

The term "prevention" as used herein means all actions that inhibit pregnancy-associated diseases or delay the onset thereof via administration of the pharmaceutical composition according to the present invention.

The term 'treatment' as used herein means all actions that alleviate or beneficially change symptoms due to pregnancy-associated diseases via administration of the pharmaceutical composition according to the present invention.

The extracellular vesicles derived from bacteria belonging to the genus *Bacillus* include either naturally or artificially secreted extracellular vesicles, and may be isolated from cultures of bacteria belonging to the genus *Bacillus*, or foods fermented with bacteria belonging to the genus *Bacillus*. Methods of isolating extracellular vesicles from the bacteria cultures or the bacteria-added fermented foods are not particularly limited as long as extracellular vesicles are isolated, and, for example, extracellular vesicles may be isolated from cultures or fermented foods by using one method selected from centrifugation, ultracentrifugation, filtration using a filter, gel filtration chromatography, free-flow electrophoresis, capillary electrophoresis, and the like, or a combination thereof. In addition, the isolation methods may further include washing for the removal of impurities, concentration of obtained extracellular vesicles, and the like.

The extracellular vesicles isolated using these methods may have an average diameter of 20 nm to 300 nm, preferably, 50 nm to 200 nm, but the present invention is not limited thereto.

The pregnancy-associated diseases of the present invention collectively refer to diseases occurring associated with pregnancy during or after pregnancy or diseases suppressed as a result of pregnancy. A representative example of the diseases occurring during pregnancy is premature delivery, and diseases, the occurrence of which is suppressed by pregnancy may be breast cancer, but the present invention is not limited thereto.

The present invention also provides a composition for inducing normal delivery which includes extracellular vesicles derived from bacteria belonging to the genus *Bacillus* as an active ingredient.

In the present invention, general characteristics of subject groups for research, i.e., pregnant women with normal delivery, pregnant women with premature delivery, and non-pregnant women as a normal control were evaluated and statistical significance thereof was analyzed. In one embodiment of the present invention, it was confirmed that, as a result of evaluation of the characteristics of subject groups for research, the normal delivery group and the premature delivery group exhibited a significant difference in gestational ages, and an apgar score was significantly low in the premature delivery group (see Example 1).

The term "apgar score" as used herein refers to a scoring system developed by Dr. Virginia Apgar, an anesthesiologist, in 1952 and used to rapidly evaluate the physical conditions of new-born babies. That is, the apgar score is a score for quantifying the effects of anesthesia on newborn babies during delivery, and the test is generally conducted at one and five minutes after birth and scoring is conducted based on five criteria: skin color; pulse rate; reflex and irritability; muscle tone; and respiration. A low score on the test conducted at 1 minute after birth shows that a newborn baby requires medical attention but does not necessarily indicate a long-term problem.

In another embodiment of the present invention, to confirm excretion of bacteria-derived extracellular vesicles via urine, extracellular vesicles derived from *Escherichia coli* as gram-negative bacteria and *Staphylococcus aureus* as gram-positive bacteria were administered to mice via muscular injection. 3 and 6 hours after injection, excretion of the extracellular vesicles via urine was confirmed. In addition, organs were extracted from the mice and as a result of analysis, it was confirmed that two types of bacteria-derived extracellular vesicles were present in the liver and the kidney (see Example 2).

In another embodiment of the present invention, based on the results of Example 2, urine samples of the normal delivery group, the premature delivery group, and non-pregnant women were collected and DNA was extracted from extracellular vesicles in the urine samples, and then metagenomic analysis was performed thereon (see Example 3).

As a result of analysis of a difference in distribution of extracellular vesicles isolated from urine samples of a normal control consisting of non-pregnant women and pregnant women, it was confirmed that a large number of extracellular vesicles derived from bacterial belonging to the genus *Pseudomonas* was distributed in the normal control, and a much larger number of extracellular vesicles derived from bacterial belonging to the genus *Bacillus* was distributed in pregnant women than in the normal control (see Example 4).

In another embodiment of the present invention, a difference between the distribution of extracellular vesicles isolated from urine samples of a normal delivery group and the distribution of extracellular vesicles isolated from urine samples of a premature delivery group was analyzed. As a result, it was confirmed that extracellular vesicles derived from bacteria of *Methylobacterium*, *Ureaplasma*, and *Veillonella* were increased in urine samples of pregnant women with premature delivery, while a great amount of extracellular vesicles derived from bacteria belonging to the genus *Bacillus* was distributed in urine samples of pregnant women with normal delivery (see Example 5).

The pharmaceutical composition according to the present invention includes extracellular vesicles derived from bacteria belonging to the genus *Bacillus* as an active ingredient, and may include a pharmaceutically acceptable carrier. The pharmaceutically acceptable carrier includes carriers commonly used for formulation, e.g., saline, sterilized water, Ringer's solution, buffered saline, cyclodextrin, dextrose solution, a maltodextrin solution, glycerol, ethanol, liposomes, and the like, but the present invention is not limited thereto, and if needed, may further include other general additives such as antioxidants, buffer solutions, and the like. In addition, preparations for injection, such as aqueous solutions, suspensions, emulsions, and the like, pills, capsules, granules, or tablets may be formulated by additionally adding a diluent, a dispersant, a surfactant, a binder, a lubricant, or the like. With regards to suitable pharmaceutically acceptable carries and formulation, preparations may be preferably formulated according to each ingredient by using a method disclosed in the Remington's reference (Remington' Pharmaceutical Science, Mack Publishing Company, Easton Pa.). Preparations of the pharmaceutical composition of the present invention are not particularly limited, but the pharmaceutical composition may be formulated into the form of injections, inhalants, external preparations for skin, and the like.

The pharmaceutical composition of the present invention may be administered orally or parenterally (e.g., intravenous administration, subcutaneous administration, intraperitoneal administration, or local administration) according to the purpose of use, and a suitable dose thereof may vary depending on conditions and body weights of patients, severity of disease, types of drugs, administration route, and administration time, but may be appropriately selected by those of ordinary skill in the art.

The composition according to the present invention is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including type of diseases of patients, the severity of disease, the activity of drugs, sensitivity to drugs, administration time, administration route, excretion rate, treatment period, and simultaneously used drugs, and factors well known in the medical field. The composition according to the present invention may be administered as an individual therapeutic agent or in combination with other therapeutic agents, may be administered consecutively or simultaneously with existing therapeutic agents, and may be administered in a single dose or multiple doses. It is important to administer the composition in the minimum amount that enables achievement of the maximum effects without side effects in consideration of all the above-described factors, and this may be easily determined by those of ordinary skill in the art.

In particular, an effective amount of the composition according to the present invention may vary according to ages, gender, and body weights of patients. Generally, the pharmaceutical composition may be administered in an amount of 0.001 mg to 150 mg, preferably, 0.01 mg to 100 mg, per body weight (1 kg) daily or every other day, or may be administered once or three times a day. However, the dosage may be increased or decreased according to administration route, the severity of obesity, gender, body weight, age, and the like, and thus the dosage is not intended to limit the scope of the present invention in any way.

According to another embodiment of the present invention, the present invention provides a method of preventing or treating pregnancy-associated diseases, the method including administering, to an individual, a pharmaceutical composition including extracellular vesicles derived from bacteria belonging to the genus *Bacillus* as an active ingredient.

The term "individual" as used herein refers to a subject with diseases requiring treatment and, more particularly, includes mammals such as humans or non-human primates, e.g., mice, rats, dogs, cats, horses, cows, and the like.

According to another embodiment of the present invention, the present invention provides a method of diagnosing premature delivery, including: extracting 16s rDNA from extracellular vesicles isolated from urine samples of pregnant women; performing polymerase chain reaction (PCR) on the 16s rDNA using a primer pair having sequences of SEQ ID NOS: 1 and 2; and determining that, in a case in which distribution of extracellular vesicles derived from bacteria belonging to the genus *Bacillus* is at least two times lower than that in normal pregnant women through sequencing of a product of the PCR, the case has a high risk of premature delivery.

In the present invention, the extracting of the 16s rDNA from extracellular vesicles isolated from urine samples of pregnant women includes: boiling the urine samples for 10 minutes to 30 minutes and then cooling the boiled urine samples; centrifuging the cooled products to obtain supernatants; and sequentially filtering the supernatants through a 0.45 μm filter and a 0.22 μm filter, but the present invention is not limited thereto.

Hereinafter, exemplary embodiments will be described to aid in understanding of the present invention. However, the following examples are provided to more easily understand the present invention and are not intended to limit the scope of the present invention.

EXAMPLES

Example 1. General Characteristics of Subject Groups for Research

In the embodiment of the present invention, from 2006 to 2008, studies on 73 non-pregnant women and 74 pregnant women (39 women with normal delivery and 35 women with premature delivery) enrolled in Dankook University and Ewha Womans University Ewha Medical Center were conducted. Non-pregnant women who received a physical examination at Dankook University Hospital were set as a normal control, and the 74 pregnant women as an experimental group were classified into a normal delivery group and a premature delivery group based on 37 weeks. Women with premature delivery who delivered a baby at less than 37 weeks at the hospital were gathered, and the normal delivery group was composed of women who received prenatal tests at the hospital and delivered a baby at a gestational age of 37 weeks or more. The enrollment criteria for pregnant women were single birth and gestational ages of 25 weeks to less than 42 weeks, and enrollment exclusion criteria were multiple births, still-born babies, congenital deformities, chronic hypertension, placental previa, and placental abruption.

The non-pregnant women and the pregnant women signed a consent form before participating in the studies, and skilled researchers collected epidemiological and clinical information of the participants. Body weight, height, and blood were collected according to standardized guidelines, and a body mass index (BMI) was calculated by dividing body weight by the square of the height ($kg/m^2$). In addition, blood was collected from the median cubital vein at night and in a fasting state and placed in EDTA tubes or serum tubes, and cholesterol, leukocyte, hemoglobin, aspartate aminotransferase, alanine aminotransferase, high density lipoprotein, fasting blood glucose, and creatinine levels were measured using an automatic analyzer (Model 7180; Hitachi, Tokyo, Japan). Clean midstream urine was used as urine samples, and was stored in sterile urine bags. In the pregnant women, when the last menstrual cycle was unclear, gestational ages were measured based on the first ultrasonic measurement, and medical records were analyzed to acquire birth information.

General characteristics of the non-pregnant women and the pregnant women are shown in Table 1 below. In the pregnant women, the normal delivery group and the premature delivery group exhibited a significant difference in gestational ages (39.73 vs. 33.57 weeks, p=0.0000), and body weights of newborn babies at birth were significantly low in the premature delivery group (3342.13 g vs. 2179.17 g, p=0.000). In addition, it was confirmed that the apgar score was significantly lower in the premature delivery group than in the normal control (p<0.05). However, gestational ages did not show a significant difference between the two groups (p>0.05).

TABLE 1

| Characteristics | Normal control (n = 72) | Pregnant women Normal delivery (n = 47) | Pregnant women Premature delivery (n = 36) | p value† |
|---|---|---|---|---|
| Age | 32.2 (12.3) | 31.96 (3.99) | 33.11 (3.75) | 0.797* |
| Gestational age | | 39.73 (1.88) | 33.57 (2.76) | 0.000 |
| Nullipara (n, %) | | 28 (59.57) | 15 (41.67) | 0.106** |
| Childbirth results | | | | |
| Birth body weight (g) | | 3342.13 (314.80) | 2179.17 (624.21) | 0.000 |
| Apgar score, 1 minute | | 9.66 (0.700) | 7.67 (2.12) | 0.000 |
| Apgar score, 5 minutes | | 9.98 (0.15) | 8.86 (1.57) | 0.000 |
| Intrauterine growth restriction (n, %) | | 0 (0.00) | 4 (2.78) | — |

Example 2. Confirmation of Excretion of Bacteria-Derived Extracellular Vesicles To confirm excretion of bacteria-derived extracellular vesicles via urine, extracellular vesicles derived from *Escherichia coli* as gram-negative bacteria and *Staphylococcus aureus* as gram-positive bacteria were administered to mice via muscular injection and were photographed every hour.

To isolate extracellular vesicles from cultures of the bacteria, first, *Escherichia coli* and *Staphylococcus aureus* were cultured on Luria-Bertani media at 30□. Subsequently, each culture was centrifuged at 5,000 g× for 30 minutes, and the supernatant was filtered through a 0.45 µm filter, and concentrated using QuixStand™ (GE Healthcare Bio-Sciences AB). The concentrated samples were filtered again via a 0.22 µm filter to isolate extracellular vesicles and then the concentration of proteins of the extracellular vesicles was measured by BCA assay (Thermo Scientific). The extracellular vesicles derived from *Escherichia coli* and *Staphylococcus aureus* were labeled with cy7 (GE Healthcare) at room temperature for 1 hour, and then administered to mice at a concentration of 20 µg/mouse via muscular injection. The mice were screened at a predetermined time using IVIS c spectrum CT (SelectScience c) at a wavelength of 780 nm to 800 nm. Organs were extracted from the mice and fluorescence thereof was measured using IVIS c spectrum CT.

As a result, as illustrated in FIG. 1A, the two types of bacteria-derived extracellular vesicles were excreted via urine 3 hours and 6 hours after injection. In addition, as illustrated in FIG. 1B, it was confirmed that, when organs were extracted 12 hours after injection, both the extracellular vesicles derived from *Escherichia coli* and the extracellular vesicles derived from *Staphylococcus aureus* were present in the liver and the kidneys. In conclusion, from the above-described results, it can be confirmed that bacteria-derived extracellular vesicles are partially excreted via urine.

Example 3. DNA Metagenomic Analysis of Extracellular Vesicles in Urine Samples 3-1. DNA Isolation from Urine DNA was isolated from extracellular vesicles present in urine samples of women with normal delivery, women with premature delivery, and non-pregnant women.

1 ml of urine of each of the normal control and the experimental groups was collected and boiled at 100□ for 15 minutes. The boiled urine samples were maintained on ice for 5 minutes and then centrifuged at 10,000 g× at 4□ for 20 minutes. Each supernatant was stored at 4□ and the quantity and quality of the isolated DNA were measured by NanoDrop before metagenomic analysis.

3-2. Metagenomic Analysis of DNA Isolated from Extracellular Vesicles in Urine

Metagenomic analysis was performed on DNA of the extracellular vesicles isolated from the urine samples of Example 3-1.

First, each clone was subjected to polymerase chain reaction (PCR) for DNA analysis by using a 16s rDNA fusion primer for the amplification of the V1-V3 region and a FastStart High Fidelity PCR System (Roche, Basel, Switzerland). Sequences of the 16s rDNA fusion primer are shown in Table 2 below.

TABLE 2

| Primer | | Sequence | SEQ ID NO: |
|---|---|---|---|
| 27F | Forward | 5'-GAGTTTGATCMTGGCTCAG-3' | 1 |
| 518R | Reverse | 5'-WTTACCGCGGCTGCTGG-3' | 2 |

*M: A or C
*W: A or T

The amplification reaction by PCR proceeded in an emulsion state (a mixed state of oil and amplicon), and microreactors including an amplification mixture and a single particle were prepared using Tissue Lyser II (Qiagen) using a GS-FLX plus emPCR Kit (454 Life Sciences). The emulsion was distributed into a 96-well plate and PCR was performed according to the manufacturer's protocol (at 94□ for 3 minutes, followed by 35 cycles at 94□ for 15 seconds, at 55□ for 45 seconds, at 72□ for 1 minute, and at 72□ for 8 minutes at the last step. 20 ng of each DNA sample was used in 50 µl PCR. Emulsion PCR (emPCR) was performed thereon to amplify each DNA, and then an amplicon was purified using an AMpure Bead kit (Beckman Coulter, Brea, Calif., USA), and quantified using a Picogreen method (Invitrogen, Carlsbad, Calif., USA). Subsequently, the amplicon was diluted and analyzed using a GS-FLX Titanium sequencer (Roche, Basel, Switzerland). After PCR amplification, the emulsion was chemically decomposed and beads with the amplified DNA library were washed via filtration. Positive beads were purified using biotinylated primer A (complementary to adaptor A) and attached to streptavidin-coated magnetic beads. Thereafter, a double helix structure of the DNA library beads attached to the magnetic beads was cleaved to be separated from the magnetic beads and single-stranded DNAs were flowed. The base sequence primer was again amplified into single-stranded DNA. Lastly, the number of beads with the amplified single-stranded DNA was counted using a Particle Counter (Beckman Coulter). Sequencing was performed on Genome Sequencer FLX titanium (454 Life Sciences), and each sample was loaded onto each of 70 mm-75 mm Pico Titer plates (454 Life Sciences).

The quality score (average Phred score>20) and read length (>300 bp) were checked for metagenomic analysis via bioinformatics and high quality sequences were collected. An operational taxonomy unit (OUT) was analyzed using UCLUST and USEARCH (Edgar, 2010), and phylogenetic classification was analyzed using QIIME (Lozupone, et al., 2006). Based on similarity, all 16s RNA sequences were classified according to the following phylogenetic steps: species >97% similarity; genus >94% similarity; family >90% similarity; order >85% similarity; class >80% similarity; phylum >75% similarity. The bacterial composition at the genus stage was drawn with a heatmap if there was a significant difference in the composition between the pregnant women and the normal control by 2 times or more. Hierarchical clustering was performed at the genus stage when there was a significant difference in composition between the pregnant women and the normal control by two times or more or there was an average composition of 1% or more.

Example 4. Analysis of Difference in Distribution of Bacteria-Derived Extracellular Vesicles Via Metagenomic Analysis DNA was isolated from extracellular vesicles in urine samples of non-pregnant women as a normal control and women with normal delivery and premature delivery as experimental groups by using the method used in Example 3-2 above and metagenomic analysis was performed thereon.

As a result, as illustrated in FIG. 2, samples were divided into a first group and a second group, and the first group was a urine sample group of pregnant women (left side) and the second group was mostly a urine sample group of the normal control (right side). The right side image illustrates a classification group showing a 2-fold or more difference between the pregnant women and the normal control and showing an average composition of 1% or more. In addition, in the case of classification without a genus name, the family (f) name or the order (o) name was used. In addition, as shown in Table 3 below, 13 classification differences were observed in the bacterial composition. The first group (pregnant women) made two clusters, and the second group (normal control) made three clusters. The first group consisted mainly of Bacillus bacteria and extracellular vesicles thereof.

TABLE 3

| Taxon | Mean of control | Mean of pregnancy | Fold change | p-value |
|---|---|---|---|---|
| Bacillus | 0.1218% | 45.6146% | 374.3878 | 1.21E−36 |
| Erythrobacteraceae(f) | 0.9847% | 2.8276% | 2.8716 | 8.47E−05 |
| Acinetobacter | 2.8650% | 1.1649% | 0.4066 | 1.05E−04 |
| Sphingomonas | 1.5396% | 0.6007% | 0.3902 | 1.57E−03 |
| Pseudomonas | 14.2252% | 4.0889% | 0.2874 | 1.21E−16 |
| Bradyrhizobiaceae(f) | 1.5951% | 0.4560% | 0.2859 | 4.14E−03 |
| Methylobacterium | 7.2819% | 1.5022% | 0.2063 | 6.79E−11 |
| Lactobacillus | 8.4385% | 1.6068% | 0.1904 | 3.11E−03 |
| Herbaspirillum | 1.9899% | 0.1409% | 0.0708 | 1.77E−07 |
| Pseudomonadaceae(f) | 15.4593% | 0.6549% | 0.0424 | 9.58E−10 |
| Atopobium | 3.8597% | 0.1017% | 0.0264 | 4.39E−03 |
| Alicyclobacillus | 3.1655% | 0.0325% | 0.0103 | 7.55E−11 |
| Alteromonadales(o) | 5.4748% | 0.0022% | 0.0004 | 1.16E−08 |

From the results of Table 3 above, it was confirmed that extracellular vesicles derived from bacteria belonging to the genus Bacillus were the most common bacteria-derived extracellular vesicles in the pregnant women (average composition=45.61%) compared to the normal control (average composition=0.12%), while extracellular vesicles derived from bacteria belonging to the genus Pseudomonas were the most common bacteria-derived extracellular vesicles in the non-pregnant women (average composition=14.23%) compared to the pregnant women (average composition=4.09%).

FIGS. 3A to 3D respectively illustrate phylum-level analysis results, class-level analysis results, order-level analysis results, and family-level analysis results of the distribution of bacteria-derived extracellular vesicles isolated from urine samples of the pregnant women (red underline) and the normal control (blue underline).

Example 5. Analysis of Difference in Distribution of Bacteria-Derived Extracellular Vesicles Between Urine Samples of Normal Delivery Group and Premature Delivery Group Metagenomic analysis was performed on DNA of the bacteria-derived extracellular vesicles isolated from urine samples of the normal delivery group and the premature delivery group of Example 3-1 by using the method used in Example 3-2. FIG. 4 illustrates the distribution of bacteria-derived extracellular vesicles isolated from urine samples of the normal delivery group and the premature delivery group. FIG. 5 illustrates summary results of the distribution of the extracellular vesicles. In addition, FIGS. 6A to 6D respectively illustrate phylum-level analysis results, class-level analysis results, order-level analysis results, and family-level analysis results of the distribution of bacteria-derived extracellular vesicles isolated from urine samples of the normal delivery group (green underline, left side) and the premature delivery group (purple underline, right side).

As a result of collective analysis of the results of FIGS. 4 to 6, it was confirmed that various types of bacteria-derived extracellular vesicles were present in the urine samples of the normal delivery group and the premature delivery group. In the urine samples of the non-pregnant women and the women with premature delivery, extracellular vesicles derived from the genus Methylobacterium were present in a large amount, while extracellular vesicles derived from bacteria belonging to the genus Bacillus were decreased. In contrast, the extracellular vesicles derived from the genus Methylobacterium was barely found in the women with normal delivery. In addition, extracellular vesicles derived from Ureaplasma bacteria and Veillonella bacteria were also more commonly found in the women with premature delivery than in the women with normal delivery.

From the above-described results, it was confirmed that unlike the cases of extracellular vesicles derived from other bacteria, extracellular vesicles derived from bacteria belonging to the genus Bacillus were present in a larger amount in women with normal delivery than in women with premature delivery.

The foregoing description of the present disclosure is provided only for illustrative purposes, and it will be understood by one of ordinary skill in the art to which the present disclosure pertains that the invention may be embodied in various modified forms without departing from the spirit or essential characteristics thereof. Thus, the embodiments described herein should be considered in an illustrative sense only and not for the purpose of limitation.

The invention claimed is:

1. A method of diagnosing premature delivery in a pregnant woman comprising:
   (A) extracting 16s rDNA from extracellular vesicles isolated from urine samples of pregnant women;
   (B) performing a polymerase chain reaction (PCR) on the 16s rDNA with a primer pair having the sequences of SEQ ID NOS: 1 and 2; and
   (C) determining a case of high risk premature delivery where distribution of extracellular vesicles derived from bacteria belonging to the genus *Bacillus* obtained from the urine samples in (A) is at least two times lower than that from urine samples of pregnant women with normal delivery, through sequencing a product of the PCR.

2. The method of claim 1, wherein the isolation of extracellular vesicles in (A) comprises:
   (a) boiling each urine sample for 10 minutes to 30 minutes and then cooling the boiled urine sample;
   (b) centrifuging the cooled product to obtain a supernatant; and
   (c) sequentially filtering the supernatant through a 0.45 μm filter and a 0.22 μm filter.

3. The method of claim 1, wherein the extracellular vesicles have an average diameter of 20 nm to 300 nm.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Forward primer for 16s rDNA

<400> SEQUENCE: 1
gagtttgatc mtggctcag                                               19

<210> SEQ ID NO 2
<211> LENGTH: 17
<212> TYPE: DNA
<213> ORGANISM: Artificial Sequence
<220> FEATURE:
<223> OTHER INFORMATION: Reverse primer for 16s rDNA

<400> SEQUENCE: 2
wttaccgcgg ctgctgg                                                 17
```